United States Patent [19]

Putzig

[11] Patent Number: 4,798,902
[45] Date of Patent: Jan. 17, 1989

[54] ZIRCONIUM CHELATES AND THEIR USE FOR CROSS-LINKING

[75] Inventor: Donald E. Putzig, Newark, Del.

[73] Assignee: E. I. Du Pont de Nemours and Company, Wilmington, Del.

[21] Appl. No.: 12,404

[22] Filed: Feb. 9, 1987

[51] Int. Cl.$^4$ .................................................. C07F 7/00
[52] U.S. Cl. .................................. 556/54; 252/8.551; 166/283; 166/305.1; 166/308
[58] Field of Search ........................................... 556/54

[56] References Cited

U.S. PATENT DOCUMENTS

| 2,824,114 | 2/1958 | Bostwick | 260/429.3 |
| 2,824,115 | 2/1958 | Beacham et al. | 556/54 X |
| 2,985,607 | 5/1961 | Koehler et al. | 556/54 X |
| 3,888,312 | 6/1975 | Tiner et al. | 166/308 |
| 4,460,751 | 7/1984 | Hanlon et al. | 525/371 |
| 4,683,068 | 7/1987 | Kucera | 556/54 X |
| 4,692,254 | 9/1987 | Kucera | 556/54 X |

FOREIGN PATENT DOCUMENTS 2108122  5/1983  United Kingdom .......... 556/54 UX

*Primary Examiner*—Paul F. Shaver
*Attorney, Agent, or Firm*—Charles E. Feeny

[57] ABSTRACT

A water-soluble zirconium chelate formed from a tetraalkyl zirconate and hydroxyethyl-tris-(hydroxypropyl) ethylene diamine, and use of the chelate as cross-linking agents in hydraulic fracturing fluids and in gels that are used for selectively plugging permeable zones in subterranean formations or for plugging subterranean leaks.

6 Claims, No Drawings

ZIRCONIUM CHELATES AND THEIR USE FOR CROSS-LINKING

BRIEF SUMMARY OF THE INVENTION

The present invention relates to a novel water-soluble zirconium chelate formed from a tetraalkyl zirconate and hydroxyethyl-tris-(hydroxypropyl) ethylene diamine. It relates also to the use of the chelate as cross-linking agents in hydraulic fracturing fluids and in gels that are used for selectively plugging permeable zones in subterranean formations or for plugging subterranean leaks.

BACKGROUND OF THE INVENTION

Water-soluble organic compounds prepared by reacting a zirconium ester with an amino alcohol are known. For example, Bostwick, in U.S. Pat. No. 2,824,114, disclosed compounds prepared by reacting an alkyl titanium or zirconium ester with a monohydric, dihydric, or trihydric monoamino or diamino alcohol, e.g., di-hydroxyethyl-ethylene diamine. Bostwick suggested using his compounds as dispersing agents and as surface active agents for hydrocarbons and waxes. Beacham et al., in U.S. Pat. No. 2,824,115, disclosed combining organo titanium and organo zirconium compounds with polyhydroxyalkyl alkylene polyamines, e.g., 0.1 mol of N,N,N',N'-tetrakis-(2-hydroxypropyl)ethylene diamine was combined with 0.1 mol of zirconium tetrachloride in 11.1 mols of water. Beacham et al. suggested that their compounds may be used as dispersing agents, additives to paint and varnish formulations to improve durability, agents for the treatment of wool and animal fibers, and in various textile and cosmetic applications.

The use of zirconium compounds as cross-linking agents is also known. An example of such use was given by Kucera in U.K. patent application GB 2 108 122 A. Kucera disclosed reacting a zirconium alkoxide with a dialkanol or trialkanol monoamine. Kucera suggested using the resulting compounds as cross-linking agents in hydraulic fracturing of subterranean formations. The production of oil and gas can be stimulated by the hydraulic fracturing technique, in which a fluid composition is introduced into an oil or gas well at a flow rate and pressure which create and/or extend a fracture into the oil- or gas-containing formation. The fluid composition usually carries a proppant (e.g., sand, bauxite, etc.) which is forced into the fracture by the fluid composition and prevents closure of the formation after the fluid pressure is released. For example, in U.S. Pat. No. 3,888,312, Tiner et al. disclosed hyraulic fracturing of subterranean formations using an aqueous gel prepared from a solvatable polysaccharide which had been cross-linked with ammonium tetralactotitanate(IV) or bis(-triethanolamine)bis(isopropyl)-titanium.

Recovery of oil from subterranean formations frequently involves displacing crude oil with a driving fluid, e.g., gas, water, brine, steam, polymer solution, foam, or micellar solution. Ideally, such techniques (commonly called flooding techniques) would provide a bank of oil of substantial depth being driven to a producing well; in practice, that frequently is not the case. Oil-bearing strata are usually heterogeneous, some parts of them being more permeable to a driving fluid than others. As a consequence, channeling frequently occurs so that the driving fluid flows preferentially through zones depleted of oil (so-called "thief" zones) rather than through those parts of the strata which contain sufficient oil to make oil-recovery operations profitable. High permeability zones can also cause undesirable loss of drilling fluids when a well (e.g., water, oil or waste disposal) is being drilled. Misplaced casing perforations or casing leaks are another cause of channeling of the driving fluid through zones of high permeability in the subterranean formations. In addition, casing leaks sometimes occur in the annular region above the injection or production packer, and need to be dealt with whether the leaks occur in high or low permeability zones.

The products of the present invention provide advantages over those of the prior art. Thus, for example, the zirconium-containing compositions of the present invention can be used at higher temperatures than the titanium-containing compositions of the prior art. The latter will decompose at elevated temperatures at which one can still use the zirconium-containing compositions of the present invention. Consequently, the zirconium-containing compositions of the present invention can be used in hotter geologic formations, including those at greater depths in oil and gas wells. In addition, the zirconium-containing compositions of the present invention are better suited as cross-linkers than are those of the prior art in cross-linked gels used in hydraulic fracturing fluids and for plugging leaks and selectively plugging permeable zones.

DETAILED DESCRIPTION OF THE INVENTION

The water-soluble zirconium chelate of the present invention can be represented by the formula:

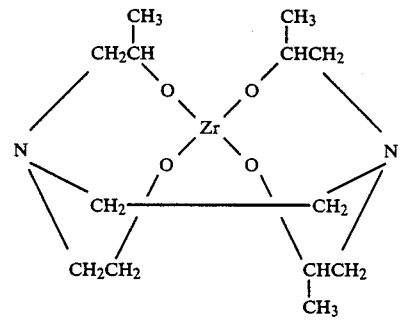

It is a reaction product of a zirconium tetraalkoxide with one molar equivalent of N-(2-hydroxyethyl)-N-(2-hydroxypropyl)-N',N'-bis-(2-hydroxypropyl)ethylene diamine. A number of zirconium tetraalkoxides (also known as tetraalkyl zirconates) can be used for the purposes of the present invention, e.g., tetra-n-propoxide, tetra-isopropoxide, and tetra-n-butoxide, with zirconium tetra-n-propoxide being preferred. The reaction of the zirconate and the ethylene diamine derivative can be carried out at a variety of temperatures, e.g., between 25 and 92 degrees C., preferably between 50 and 70 degrees C.

In the hydraulic fracturing process of this invention, one or more fractures is created or extended in an oil- or gas-containing subterranean formation by introducing a cross-linked gel formed from a solvatable polysaccharide into the formation at a flow rate and pressure sufficient to create or extend such a fracture. Another embodiment of the present invention relates to a process for selectively plugging permeable zones in subterranean formations or for plugging subterranean leaks which comprises injecting into the permeable zone or the site of the subterranean leak a cross-linked gel formed from a solvatable polysaccharide. The cross-linking agent for each process is one of the zirconate/-substituted ethylene diamine compositions described above.

The solvatable polysaccharides include guar gum and locust bean gum, as well as other galactomannan and glucomannan gums, such as those derived from sennas, Brazilwood, Tera, Honey locust, Karaya gum and the like. Derivatives of such gums are useful also, e.g., hydroxyethylguar, hydroxypropylguar, carboxyethylhydroxyethylguar, carboxymethylhydroxypropylguar, and the like, as well as cellulose derivatives containing carboxyl groups, such as carboxymethylcellulose, carboxymethylhydroxyethylcellulose, and the like. Hydroxypropylguar and carboxymethylhydroxypropylguar are preferred polysaccharides for use in the present invention. Hydroxypropylguar is the most preferred gum based upon its commercial availability and desirable properties. On the other hand, carboxymethylhydroxypropylguar is sometimes used in place of hydroxypropylguar in fracturing fluids when the permeability of the formation is such that one wishes to keep the residual solids at a low level, so as to prevent formation damage. The solvatable polysaccharides can be used individually or in combination; usually, however, a single material is used. The solvatable polysaccharides are normally blended with a solvent such as water or an aqueous medium (e.g., aqueous methanol, ethanol, 1 to 3% HCl or potassium chloride) to form an uncross-linked gel as a first step.

The amounts of solvatable polysaccharide and the cross-linker therefor vary. One uses small but effective amounts which for both will vary with the circumstances, e.g., the type of geologic formation, the depth at which the process (e.g., fluid fracturing, permeable zone plugging or leak plugging) is to be performed, temperature, pH, etc. In all cases, one uses as small an amount of each in water as will provide the viscosity level necessary to effect the desired result, i.e., fracturing of the subterranean formation, or plugging leaks or permeable zones to the extent necessary to promote adequate recovery of oil or gas from it. For example, satisfactory gels can generally be made for fluid fracturing by using the solvatable polysaccharide in amounts up to about 1.5 weight percent and up to about 0.10 weight percent of the cross-linker, both percentages being based on the weight of the aqueous liquid. Preferably, from about 0.4 to about 0.75 weight percent of the solvatable polysaccharide is used and from about 0.045 to about 0.075 weight percent of the cross-linker. For plugging leaks or permeable geologic zones, one generally uses about 0.40 to 1.2 weight percent of a solvatable polysaccharide, preferably 0.5 to 0.75 weight percent, and 0.04 to 0.12 weight percent of the zirconium chelate, preferably 0.05 to 0.075 weight percent.

The following Examples are given in further illustration of the invention but not by way of limitation. The Control exemplifies the type of composition which one would obtain by following the synthesis described by Beacham et al. in Example 4 of U.S. Pat. No. 2,824,115. Preparation of the compositions in the Examples and in the Control were each carried out in a closed vessel containing an agitator, thermometer, condenser, nitrogen inlet and dropping funnel. Unless specified otherwise, percentages are given by weight. Temperatures are given in degrees Celsius. The cross-linking properties of the compositions of this invention are given in the Examples as a function of the viscosity of hydroxypropylguar cross-linked with the zirconate of this invention. For a pH 7 gel, one blends for 30 minutes in a Waring Blender at a pH of 7: a fumaric acid/sodium bicarbonate buffer, 4.5 g of hydroxypropylguar and 0.9 g of sodium thiosulfate in 750 ml of 2% by weight KCl. If one wants a pH of 8.6 gel, the fumaric acid is omitted. Unless specified otherwise, a pH 8.6 gel is used in the Examples. To any such gel in a 1500 ml beaker one adds 0.42 ml of cross-linker solution containing 0.00064 mol of zirconium (hereinafter referred to as the Standard Loading Density) and mix vigorously for about 15-180 seconds. A 25 ml sample of that cross-linker containing gel is placed in the cup of the FANN 50 Viscometer with an R-1, B-3 configuration at 250 degrees F (121 decrees C) and 100 rpm (88 sec$^{-1}$) shear.

EXAMPLE 1

N-(2-hydroxyethyl)-N-(2-hydroxypropyl)-N',N'-bis-(2-hydroxypropyl)-ethylene diamine (37.2 g - 0.133 m) was added to 56.5 g (0.133 m) of zirconium tetra-n propoxide solution in n-propanol (21.5% Zr). The mixture was heated to 50 degrees C±10 degrees C. and held for 2 hours. Yield =93.7 g of a pale yellow liquid containing about 13% Zr and having a density of 1.06 g/ml. Cross-linking characteristics of the product are given in Tables 1 and 2.

TABLE 1

| pH | Cross-linking Rate (sec) |
|---|---|
| 3.5 | 23 |
| 5.0 | 77 |
| 7.0 | >180 |
| 8.5 | >180 |
| 10.0 | >180 |

TABLE 2

| Time (min) | Viscosity (cps) |
|---|---|
| 0 | 150 |
| 5 | 360 |
| 10 | 264 |
| 20 | 222 |
| 30 | 213 |
| 40 | 201 |
| 60 | 162 |
| 90 | 115 |

CONTROL 1

Example IV of U.S. Pat. No. 2,824,115 was repeated as follows. A solution of zirconium tetrachloride (46.6 g –0.2 mol) in water (400 ml –22.2 mols) was added with stirring to QUADROL N,N,N',N'-tetrakis-(2-hydroxypropyl)-ethylene diamine (58.4 g–0.2 mol) at 25 degrees. Heat was evolved and the reaction mixture was cooled to 25 degrees. A white precipitate formed. The pH of the resulting slurry was adjusted to 12 with a 14% aqueous solution of sodium hydroxide (32 g NaOH in 200 ml of water). The reaction mass remained in the form of a white slurry. As a consequence, it could not be used as a cross-linking agent, since a soluble agent is necessary for that purpose.

EXAMPLE 2

The procedure of EXAMPLE 1 was repeated with 63.1 g (0.227 mol) of the same diamine derivative and zirconium tetra-n-butoxide (100 g–0.227 mol) in n-butanol. The resulting pale yellow liquid was heated to 60 degrees C. and held for 2 hours, giving 162 g of a clear yellow liquid product having a density of 1.06.

What is claimed is:

1. A zirconium diamine chelate represented by the formula:

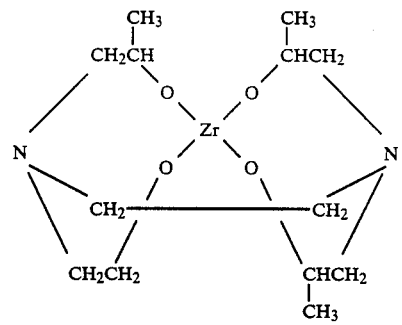

2. A process for preparing the zirconium chelate of claim 1 which comprises reacting a tetraalkyl zirconate with 1 molar equivalent of N-(2-hydroxy-ethyl)-N-(2-hydroxypropyl)-N',N'-bis-(2-hydroxypropyl) ethylene diamine.

3. A process of claim 2 wherein said zirconate is tetrakis(n-propyl) zirconate.

4. A liquid composition consisting essentially of the chelate of claim 1 dissolved in an alkanol.

5. The liquid composition of claim 4 wherein said alkanol is that generated in synthesizing said chelate from a tetraalkyl zirconate and N-(2-hydroxyethyl)-N-(2-hydroxypropyl)-N',N'-bis-(2-hydroxypropyl)ethylene diamine.

6. The composition of claim 5 wherein said alkanol is n-propanol.

* * * * *